(12) United States Patent
Tirinato et al.

(10) Patent No.: US 8,831,983 B2
(45) Date of Patent: *Sep. 9, 2014

(54) POINT-OF-CARE INVENTORY MANAGEMENT SYSTEM AND METHOD

(75) Inventors: Jody Ann Tirinato, Plainsboro, NJ (US); Michael P Zelin, Plainsboro, NJ (US); Paul Andrew Gibson, Metuchen, NJ (US); Lyudmila Zaltsman, Princeton, NJ (US); Graham Davis, Princeton, NJ (US)

(73) Assignee: Abbott Point of Care Inc., Princeton, NJ (US)

( * ) Notice: Subject to any disclaimer, the term of this patent is extended or adjusted under 35 U.S.C. 154(b) by 113 days.

This patent is subject to a terminal disclaimer.

(21) Appl. No.: 13/051,520

(22) Filed: Mar. 18, 2011

(65) Prior Publication Data

US 2011/0166427 A1     Jul. 7, 2011

Related U.S. Application Data

(60) Continuation of application No. 12/428,969, filed on Apr. 23, 2009, now Pat. No. 7,912,754, which is a division of application No. 11/761,142, filed on Jun. 11, 2007, now Pat. No. 7,552,071, which is a continuation of application No. 10/384,820, filed on Mar. 11, 2003, now Pat. No. 7,263,501.

(51) Int. Cl.
*G06Q 10/00* (2012.01)
*G06Q 20/20* (2012.01)
*G06Q 30/02* (2012.01)
*G06Q 10/08* (2012.01)
*G06Q 30/06* (2012.01)

(52) U.S. Cl.
CPC ............ *G06Q 10/087* (2013.01); *G06Q 20/203* (2013.01); *G06Q 30/0223* (2013.01); *Y10S 707/99931* (2013.01); *G06Q 30/0639* (2013.01)
USPC ........... 705/28; 705/14.24; 705/22; 705/26.9; 362/101; 360/27; 707/999.001

(58) Field of Classification Search
None
See application file for complete search history.

(56) References Cited

U.S. PATENT DOCUMENTS

| 4,135,241 A | 1/1979 | Stanis et al. |
| 4,636,950 A | 1/1987 | Caswell et al. |

(Continued)

FOREIGN PATENT DOCUMENTS

| EP | 1277438 A1 | 1/2003 |
| JP | 2001-198194 | 7/2001 |

(Continued)

OTHER PUBLICATIONS

Office Action for Japanese Appl. No. 2006-507047 dated Mar. 16, 2010.

(Continued)

*Primary Examiner* — Fateh Obaid

(57) ABSTRACT

A system and method are disclosed for controlling an inventory of point-of-care diagnostic devices. The inventory includes a main inventory and at least one subinventory. Each device has an ambient temperature shelf life. Data associated with the devices is entered, including: the current quantity and predetermined minimum quantity of devices in the main inventory; and the current quantity and predetermined minimum quantity of devices in the subinventory. A first timestamp is associated with each device when the device is transferred from the main inventory to the ambient temperature subinventory. The first timestamp is compared to a second timestamp prior to use of the device to determine whether the device's ambient temperature shelf life is exceeded. The current quantity of devices in the subinventory is updated in response to an event that causes a change in the current quantity of devices in the subinventory.

5 Claims, 9 Drawing Sheets

(56) References Cited

U.S. PATENT DOCUMENTS

| | | | |
|---|---|---|---|
| 4,688,026 A | 8/1987 | Scribner et al. | |
| 4,737,910 A | 4/1988 | Kimbrow | |
| 4,933,048 A | 6/1990 | Lauks | |
| 4,943,939 A | 7/1990 | Hoover | |
| 4,954,087 A | 9/1990 | Lauks et al. | |
| 4,967,928 A | 11/1990 | Carter | |
| 5,065,315 A | 11/1991 | Garcia | |
| 5,096,669 A | 3/1992 | Lauks et al. | |
| 5,112,455 A | 5/1992 | Cozzette et al. | |
| 5,124,661 A | 6/1992 | Zelin et al. | |
| 5,168,445 A | 12/1992 | Kawashima et al. | |
| 5,178,417 A | 1/1993 | Eshoo | |
| 5,200,051 A | 4/1993 | Cozzette et al. | |
| 5,305,199 A | 4/1994 | LoBiondo et al. | |
| 5,310,997 A | 5/1994 | Roach et al. | |
| 5,332,315 A | 7/1994 | Baker et al. | |
| 5,374,813 A | 12/1994 | Shipp | |
| 5,380,994 A | 1/1995 | Ray | |
| 5,382,784 A | 1/1995 | Eberhardt | |
| 5,434,775 A | 7/1995 | Sims et al. | |
| 5,442,669 A | 8/1995 | Medin | |
| 5,447,440 A | 9/1995 | Davis et al. | |
| 5,485,250 A | 1/1996 | Kashimura et al. | |
| 5,495,250 A | 2/1996 | Ghaem et al. | |
| 5,542,420 A | 8/1996 | Goldman et al. | |
| 5,548,110 A | 8/1996 | Storch et al. | |
| 5,595,356 A | 1/1997 | Kewin | |
| 5,597,995 A | 1/1997 | Williams et al. | |
| 5,638,519 A | 6/1997 | Haluska | |
| 5,640,002 A | 6/1997 | Ruppert et al. | |
| 5,646,389 A | 7/1997 | Bravman et al. | |
| 5,675,744 A | 10/1997 | Tsujii | |
| 5,752,234 A | 5/1998 | Withers | |
| 5,781,442 A | 7/1998 | Engleson et al. | |
| 5,790,409 A | 8/1998 | Fedor et al. | |
| 5,812,986 A | 9/1998 | Danelski | |
| 5,838,253 A | 11/1998 | Wurz et al. | |
| 5,845,264 A | 12/1998 | Nellhaus | |
| 5,887,176 A * | 3/1999 | Griffith et al. | 713/320 |
| 5,912,818 A | 6/1999 | McGrady et al. | |
| 5,949,335 A | 9/1999 | Maynard | |
| 5,953,234 A | 9/1999 | Singer et al. | |
| 5,953,707 A | 9/1999 | Huang et al. | |
| 5,963,134 A | 10/1999 | Bowers et al. | |
| 5,991,728 A | 11/1999 | DeBusk et al. | |
| 5,993,046 A | 11/1999 | McGrady et al. | |
| 5,995,937 A | 11/1999 | DeBusk et al. | |
| 5,996,889 A | 12/1999 | Fuchs et al. | |
| 6,018,713 A | 1/2000 | Coli et al. | |
| 6,042,264 A * | 3/2000 | Prusik et al. | 374/106 |
| 6,059,544 A | 5/2000 | Jung et al. | |
| 6,098,892 A | 8/2000 | Peoples, Jr. | |
| 6,108,588 A | 8/2000 | McGrady | |
| 6,151,536 A | 11/2000 | Arnold et al. | |
| 6,155,975 A | 12/2000 | Urich et al. | |
| 6,170,746 B1 | 1/2001 | Brook et al. | |
| 6,188,990 B1 | 2/2001 | Brook et al. | |
| 6,195,006 B1 | 2/2001 | Bowers et al. | |
| 6,223,137 B1 | 4/2001 | McCay et al. | |
| 6,232,876 B1 | 5/2001 | Maloney | |
| 6,238,623 B1 | 5/2001 | Amhof et al. | |
| 6,249,774 B1 | 6/2001 | Roden et al. | |
| 6,260,761 B1 | 7/2001 | Peoples, Jr. | |
| 6,339,732 B1 | 1/2002 | Phoon et al. | |
| 6,357,662 B1 | 3/2002 | Helton et al. | |
| 6,366,890 B1 | 4/2002 | Usrey | |
| 6,379,883 B2 | 4/2002 | Davis et al. | |
| 6,381,576 B1 | 4/2002 | Gilbert | |
| 6,415,978 B1 | 7/2002 | McAllister | |
| 6,438,498 B1 | 8/2002 | Opalsky et al. | |
| 6,519,569 B1 | 2/2003 | White et al. | |
| 6,532,399 B2 | 3/2003 | Mase | |
| 6,542,902 B2 | 4/2003 | Dulong et al. | |
| 6,557,758 B1 | 5/2003 | Monico | |
| 6,597,969 B2 | 7/2003 | Greenwald et al. | |
| 6,611,846 B1 | 8/2003 | Stoodley | |
| 6,632,654 B1 | 10/2003 | Gebrian et al. | |
| 6,636,780 B1 | 10/2003 | Haitin et al. | |
| 6,640,159 B2 | 10/2003 | Holmes et al. | |
| 6,648,223 B2 | 11/2003 | Boukhny et al. | |
| 6,664,887 B1 | 12/2003 | Fuchs | |
| 6,718,285 B2 | 4/2004 | Schwartz et al. | |
| 6,758,403 B1 | 7/2004 | Keys et al. | |
| 6,763,996 B2 | 7/2004 | Rakers et al. | |
| 6,795,376 B2 | 9/2004 | Quine | |
| 6,801,913 B2 | 10/2004 | Matsumura et al. | |
| 6,915,170 B2 | 7/2005 | Engleson et al. | |
| 6,924,148 B2 | 8/2005 | Prusik | |
| 6,959,862 B2 | 11/2005 | Neumark | |
| 6,967,563 B2 | 11/2005 | Bormaster | |
| 6,985,408 B2 | 1/2006 | Quine | |
| 7,596,426 B2 | 9/2009 | McGrady et al. | |
| 2002/0050833 A1 * | 5/2002 | Jones et al. | 324/760 |
| 2002/0077850 A1 | 6/2002 | McMenimen et al. | |
| 2002/0188499 A1 | 12/2002 | Jenkins et al. | |
| 2003/0004750 A1 | 1/2003 | Teraoka et al. | |
| 2003/0019165 A1 | 1/2003 | Gallant et al. | |
| 2003/0023501 A1 | 1/2003 | Alling | |
| 2003/0023503 A1 | 1/2003 | Alling | |
| 2003/0101107 A1 | 5/2003 | Agarwal et al. | |
| 2003/0110104 A1 | 6/2003 | King et al. | |
| 2003/0172009 A1 | 9/2003 | Katou | |
| 2003/0195770 A1 | 10/2003 | Fukushima | |
| 2004/0158507 A1 | 8/2004 | Meek et al. | |
| 2004/0162768 A1 | 8/2004 | Snyder et al. | |
| 2004/0173456 A1 * | 9/2004 | Boos et al. | 204/403.02 |
| 2004/0195309 A1 | 10/2004 | Wagner et al. | |
| 2006/0143047 A1 | 6/2006 | Briegs et al. | |
| 2009/0119047 A1 * | 5/2009 | Zelin et al. | 702/82 |
| 2009/0177516 A1 | 7/2009 | Birjandi et al. | |
| 2010/0009343 A1 * | 1/2010 | Fischer et al. | 435/5 |

FOREIGN PATENT DOCUMENTS

| | | |
|---|---|---|
| JP | 2002-251456 | 9/2002 |
| JP | 2003-058640 | 2/2003 |
| JP | 2003-533706 | 11/2003 |
| JP | 2004-503271 | 2/2004 |
| JP | 2004-512245 | 4/2004 |
| JP | 2005-514965 | 5/2005 |
| JP | 2008-508359 | 3/2008 |
| WO | WO 01/88634 | 11/2001 |
| WO | WO 02/05039 | 1/2002 |
| WO | WO 02/19193 | 3/2002 |
| WO | WO 02/35432 | 5/2002 |
| WO | WO 02/095675 | 11/2002 |
| WO | WO 03017058 A2 | 2/2003 |

OTHER PUBLICATIONS

Supplementary European Search Report for EP Application No. 04 71 9716, dated Oct. 6, 2006 (3 pages).

Derfler Frank J., et al., How Networks Work, 6th Ed., Que Corporation, Oct. 4, 2002.

White, Ron, How Computers Work, 6th Ed., Que Corporation, Sep. 10, 2001.

Gralla, Preston, How the Internet Works, 6th Ed. Que Corporation, Sep. 7, 2001.

Chopra, Sunil, et al., Supply Chain Management, Strategy, Planning & Operation, Prentice-Hall, Inc. Oct. 10, 2000.

Derfler, Frank J., et al., How Networks Work, Millennium Ed., Que Corporation, Aug. 23, 2000.

Gralla. Preston, How the Internet Works, Millennium Ed., Que Corporation, Sep. 23, 1999.

White, Ron, How Computers Work, Millennium Ed., Que Corporation, Sep. 22, 1999.

Bragg, Steven M., Accounting Best Practices, John Wiley and Sons, Inc., 1999.

Muller, Nathan J., Desktop Encyclopedia of the Internet, Artech House, Inc., 1998.

(56) References Cited

OTHER PUBLICATIONS

Greene, James H., Editor-in-Chief, Production and Inventory Control Handbook, 3rd Ed., The McGraw-Hill Companies, Inc., 1997.
Dobler, Donald w., et al., Purchasing and Supply Management, Text & Cases, 6th Ed., The McGraw-Hili Companies, Inc., 1996.
Zhaotong Lian, Liming Liu; Studies, Inventory Management, Perishable Goods, Markov Analysis, Batch Processing, Heuristic, Mathematical Models; IIE Transactions. Norcross: Sep. 2001. vol. 33, Iss. 9; p. 809, 14 pgs; http://Proquest.umi.com/pdqweb?did+77081955&sid=13&Fmt=2&clientId=19649&RQT=309&VName=PQD.

* cited by examiner

FIG. 1

| Location/Cartridge | ER | CCU | PICU | ICU | RDU | OR | CVOR | GW |
|---|---|---|---|---|---|---|---|---|
| Type 1 | 200 | 100 | 100 | 200 | | 100 | 100 | |
| Type 2 | 250 | 250 | 250 | 250 | | 500 | 500 | |
| Type 3 | 50 | 50 | 50 | 50 | | 100 | 100 | |
| Type 4 | 50 | 50 | 50 | 50 | | 100 | 100 | |
| Type 5 | 100 | 200 | 200 | 400 | 100 | | | |
| Type 6 | 100 | 100 | 100 | 100 | | | | |
| Type 7 | 500 | 500 | 500 | 500 | | 500 | 500 | |
| Type 8 | | 100 | 100 | 200 | | | | |
| Type 9 | 200 | 100 | 100 | 100 | | 100 | | 200 |

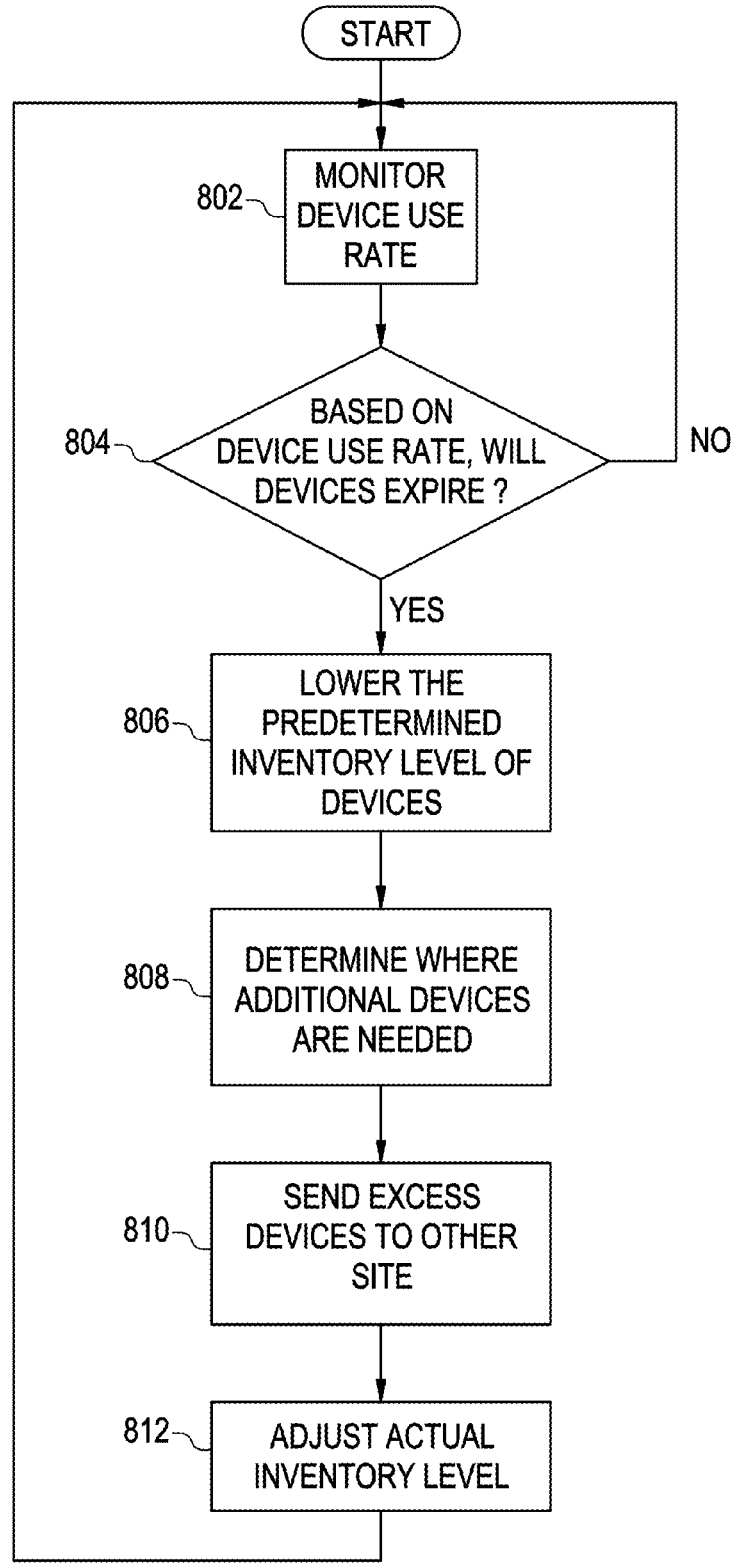

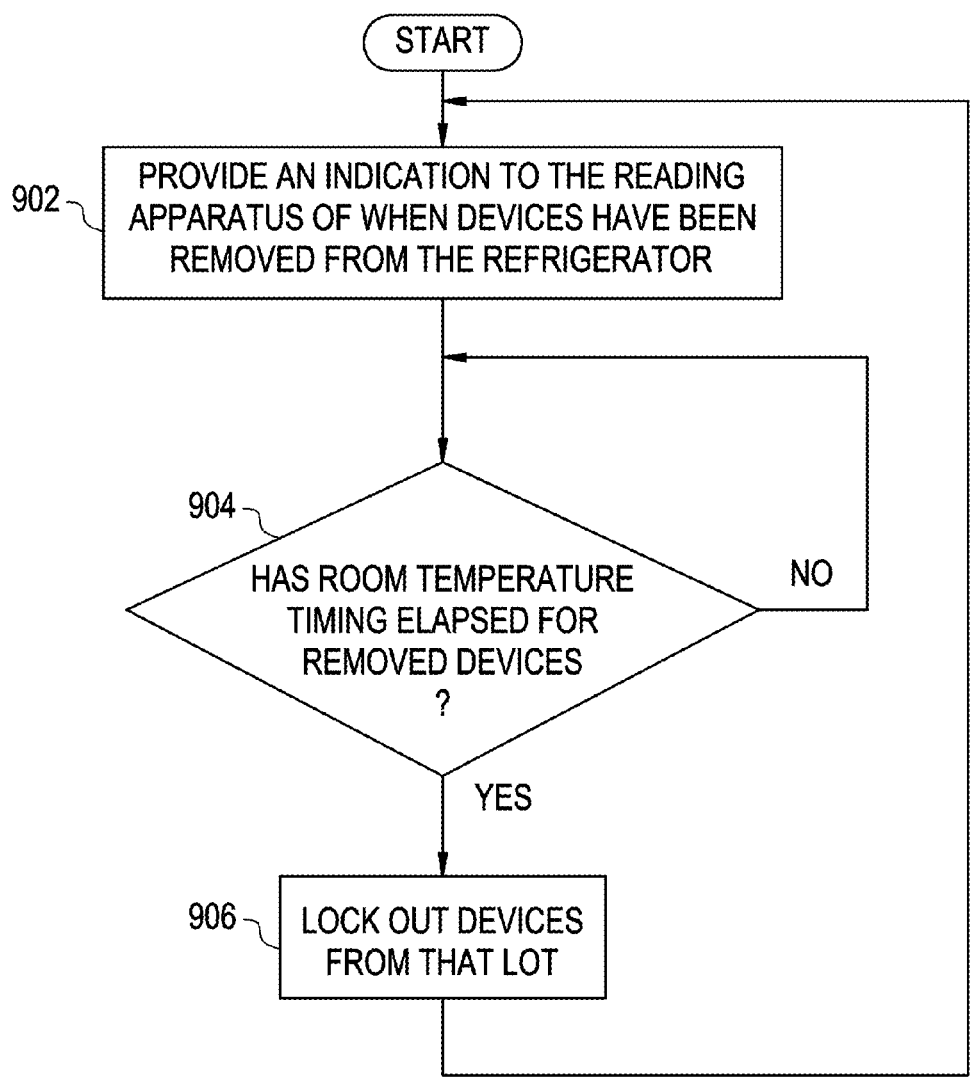

POINT-OF-CARE INVENTORY MANAGEMENT SYSTEM AND METHOD

The present application is a continuation of U.S. patent application Ser. No. 12/428,969, filed Mar. 23, 2009, which is a divisional of U.S. patent application Ser. No. 11/761,142, filed Jun. 11, 2007, now U.S. Pat. No. 7,552,071, which is a continuation of U.S. patent application Ser. No. 10/384,820, filed Mar. 11, 2003, now U.S. Pat. No. 7,263,501, the entire contents of which are hereby incorporated by reference herein.

BACKGROUND

1. Field of the Invention

The present invention relates to a method and apparatus for inventory control, specifically to disposable elements and general consumable items that are used in a hospital or medical facility, and more specifically to point-of-care sample analysis systems that use different types of disposable devices.

2. Background Information

For hospitals, the recent introduction of point-of-care testing capabilities has created unique requirements for inventory control. The inventory control requirements arise from the use of multiple types of disposable sample testing devices at various locations within a hospital. The hospital must provide an adequate supply of each type of device at each site of use. However, the hospital tries to be mindful of the cost of carrying excess inventory at each site. This is also true for other locations where point-of-care testing occurs, such as military combat sites, cruise ships and nursing homes.

Certain sample testing devices have a finite shelf-life, in which the shelf-life may depend upon whether the sample testing device is refrigerated or maintained at ambient or room temperature, e.g., room temperature for a hospital. For example, a blood testing device may have a shelf-life of six to nine months when refrigerated, or a limited shelf-life of two weeks at ambient temperature. Because of the differences in shelf-life, a hospital will generally store devices at a central refrigerated location, and deliver devices to specific departments as demand requires. These departments may or may not have available refrigerated storage, which consequently affects the inventory they will maintain. In certain departments, general storage may be limited, which will also affect what level of inventory they maintain.

Point-of-care sample analysis systems are generally based on a re-usable reading apparatus that performs sample tests using a disposable device, e.g., a cartridge or strip, that contains analytical elements, e.g., electrodes or optics for sensing analytes such as, for example, pH, oxygen and glucose. The disposable device can optionally include fluidic elements (e.g., conduits for receiving and delivering the sample to the electrodes or optics), calibrant elements (e.g., aqueous fluids for standardizing the electrodes with a known concentration of the analyte), and dyes with known extinction coefficients for standardizing optics. The reading apparatus contains the electrical circuitry and other components for operating the electrodes or optics, making measurements, and doing computations. The reading apparatus also has the ability to display results and communicate those results to laboratory and hospital information systems (LIS and HIS, respectively), for example, via a computer workstation. Communication between the reading apparatus and a workstation, and between the workstation and a LIS, can be via, for example, an infrared link, a wired connection, wireless communication, or any other form of data communication that is capable of transmitting and receiving electrical information, or any combination thereof.

One benefit of point-of-care sample testing systems is the elimination of the time-consuming need to send a sample to a central laboratory for testing. Point-of-care sample testing systems allow a nurse, at the bedside of a patient, to obtain a reliable, quantitative, analytical result, comparable in quality to that which would be obtained in a laboratory. In operation, the nurse selects a device with the required panel of tests, draws a sample, dispenses it into the device, optionally seals the device with, for example, a snap-closure, and inserts the device into the reading apparatus. While the particular order in which the steps occur may vary between different point-of-care systems and providers, the intent of providing rapid sample test results close to the location of the patient remains. The reading apparatus then performs a test cycle, i.e., all the other analytical steps required to perform the tests. Such simplicity gives the physician quicker insight into a patient's physiological status and, by reducing the time for diagnosis, enables a quicker decision by the physician on the appropriate treatment, thus enhancing the likelihood of a successful patient treatment.

In the emergency room and other acute-care locations within a hospital, the types of sample tests required for individual patients tend to vary. Thus, point-of-care systems generally offer a range of disposable devices with different sample tests, or combinations of sample tests. For example, for blood analysis devices, in addition to traditional blood tests, including oxygen, carbon dioxide, pH, potassium, sodium, chloride, hematocrit, glucose, urea, creatinine and calcium, other tests can include, for example, prothrombin time (PT), activated clotting time (ACT), activated partial thromboplastin time (APTT), troponin, creatine kinase MB (CKMB) and lactate. While devices typically contain between one and ten tests, it will be appreciated by persons of ordinary skill in the art that any number of test may be contained on a device. For example, a device for genetic screening may include numerous tests. To illustrate the need for different devices, a patient suspected of arrhythmia may require a device with a test combination that includes a potassium test, whereas a patient suspected of a diabetic coma may require a device with a test combination that includes a glucose test. An emergency room will need to have sufficient inventory of both types of device to ensure the supply meets the anticipated workload, while seeking to limit the economic cost associated with carrying an unnecessarily high inventory.

A given hospital may use numerous different types of devices and accordingly needs to maintain a combination of some or all of these at each point-of-care testing location within the hospital. These locations can include, for example, an emergency room (ER), a critical care unit (CCU), a pediatric intensive care unit (PICU), an intensive care unit (ICU), a renal dialysis unit (RDU), an operating room (OR), a cardiovascular operating room (CVOR), general wards (GW) and the like. Other hospital locations can be used to deliver point-of-care testing, as can other non-hospital-based locations where medical care is delivered, including, for example, MASH units, nursing homes, and cruise, commercial and military ships, and the like. FIG. 1 depicts an example of monthly device consumption rates at different locations in a hospital versus the different available device types. It will be appreciated by persons of ordinary skill in the art that the demand for particular devices may vary significantly between locations within, for example, a hospital.

Previously, inventory control of devices at the point-of-care relied on direct human intervention. Typically, personnel in the emergency room and/or other locations would call the hospital laboratory, where disposable devices are usually centrally stored to place an order. Alternatively, the hospital laboratory can control the disposable device storage at a central repository. The hospital laboratory would then request additional devices of specific types to be delivered to the requesting department. The central repository would then arrange for the devices to be delivered. Alternatively, a person from the laboratory, e.g., a designated point-of-care testing coordinator, would be responsible for regularly visiting point-of-care testing locations, checking device inventory needs and ensuring that those needs are met. Because of the manual nature of this inventory control scheme, there are several opportunities for delay and possible human error.

Once devices are delivered from the central repository, the devices can be stored at a convenient location, e.g., somewhere close to the patient. The convenient location will vary by department, but can include, for example, at the patient bedside (e.g., when the reading apparatus is part of a patient monitoring system), at a nursing station, in an auxiliary room attached to a ward, in a satellite laboratory attached to a critical care unit, and the like. One skilled in the art will recognize that where devices are stored at the bedside, the devices are unlikely to be refrigerated, whereas devices stored in a satellite laboratory may be refrigerated.

Typically, devices are supplied by the manufacture to the hospital in boxes with a given number of units, e.g., 25 or 50 units, or any number of units. The central repository in the hospital can supply these devices to the different departments in boxes or individually. Thus, the minimum inventory level for a department can be set in terms of the number of available unopened boxes of devices or on an absolute number of available individual devices.

Current inventory control systems and methods for handling point-of-care device inventory place the end-user, usually a nurse, at the center of the process. Essentially, the end user had to log or visually monitor the number of boxes of each type of device at their location and call the central repository to order more, as they see fit. Alternatively, a person from the laboratory was responsible for coordinating point-of-care testing by making regular visits to each site and ensuring devices are delivered when needed.

Thus, in creating the new environment of point-of-care sample testing, where a nurse performs sample tests at or close to the bedside of the patient, many of the previous problems associated with delay due to sample transportation to a hospital laboratory for analysis have been solved. The following patents relating to point-of-care sample testing are assigned to the same assignee as the present application: DISPOSABLE SENSING DEVICE FOR REAL TIME FLUID ANALYSIS, Lauks et al., U.S. Pat. No. 5,096,669; WHOLLY MICROFABRICATED BIOSENSORS AND PROCESS FOR THE MANUFACTURE AND USE THEREOF, Cozzette et al., U.S. Pat. No. 5,200,051; METHOD FOR ANALYTICALLY UTILIZING MICROFABRICATED SENSORS DURING WET-UP, Cozzette et al., U.S. Pat. No. 5,112,455; SYSTEM, METHOD AND COMPUTER IMPLEMENTED PROCESS FOR ASSAYING COAGULATION IN FLUID SAMPLES, Opalsky et al., U.S. Pat. No. 6,438,498; MICROFABRICATED APERTURE-BASED SENSOR, Davis et al., U.S. Pat. No. 6,379,883; APPARATUS FOR ASSAYING VISCOSITY CHANGES IN FLUID SAMPLES AND METHOD OF CONDUCTING SAME, Davis et al., U.S. Pat. No. 5,447,440; REUSABLE TEST UNIT FOR SIMULATING ELECTROCHEMICAL SENSOR SIGNALS FOR QUALITY ASSURANCE OF PORTABLE BLOOD ANALYZER INSTRUMENTS, Zelin et al., U.S. Pat. No. 5,124,661; STATIC-FREE INTERROGATING CONNECTOR FOR ELECTRICAL COMPONENTS, Lauks, U.S. Pat. No. 4,954,087; and REFERENCE ELECTRODE, METHOD OF MAKING AND METHOD OF USING SAME, Lauks, U.S. Pat. No. 4,933,048.

However, new inventory management issues were created as a consequence of the transition to point-of-care sample analysis.

SUMMARY OF THE INVENTION

A system and method are disclosed for controlling an inventory of a plurality of point-of-care diagnostic devices. The plurality of devices includes at least one type of device. Each device is configured to perform at least one sample analysis, and each device has a usable lifetime. The inventory includes a main inventory and at least one subinventory. Each subinventory is associated with a point-of-care location. According to a first aspect of the present invention, the inventory control system comprises a data input interface for entering data associated with the devices and a data output interface for displaying data associated with the devices. The data can include a current number of at least one type of device in the main inventory and a predetermined minimum number of devices of that type in the main inventory, and can include a current number of at least one type of device in the at least one subinventory and a predetermined minimum number of devices of that type in the at least one subinventory. A memory stores data associated with the devices and stores steps of a computer program to automatically update the current number of devices in the at least one subinventory in response to an occurrence of an event that causes a change in the current number of devices in the at least one subinventory. For example, the event can include at least one of (i.) a device from the at least one subinventory is used to perform at least one sample analysis, (ii.) a device from the at least one subinventory is transferred to another subinventory, and (iii.) a device from the at least one subinventory exceeds the usable lifetime of the device. The inventory control system also includes a processor for accessing the memory to execute the computer program.

According to a second aspect of the present invention, a method for controlling an inventory of a plurality of point-of-care sample analysis devices, wherein the inventory includes a main inventory and at least one subinventory, wherein the plurality of devices includes at least one type of device, wherein each device is configured to perform at least one sample analysis, and wherein each device has a usable lifetime, comprises the steps of: (i.) entering data associated with the devices, wherein the data includes a current number of at least one type of device in the main inventory and a predetermined minimum number of devices of that type in the main inventory, and includes a current number of at least one type of device in the at least one subinventory and a predetermined minimum number of devices of that type in the at least one subinventory, wherein each of the at least one subinventory is associated with a point-of-care location; and (ii.) automatically updating the current number of devices in the at least one subinventory in response to an occurrence of an event that causes a change in the current number of devices in the at least one subinventory.

According to a third aspect of the present invention, a method for distributing devices having a finite usable lifetime, the devices being contained within an inventory of devices, comprises the steps of: (i.) determining an inventory level of devices in the inventory of a first location, in response to an occurrence of an event that causes a change in a current number of devices in the inventory; (ii.) computing a device usage rate for the first location; (iii.) determining an excess device differential based on the device usage rate and the inventory level, wherein the excess device differential represents the devices that will remain in the inventory at the expiration of the usable lifetime; and (iv.) transferring the excess device differential to a second location. According to the alternative exemplary embodiment, a predetermined inventory level represents a minimum number of devices contained in the inventory. The method can further comprise the steps of (v.) adjusting the predetermined inventory level based on the device usage rate, and (vi.) adjusting the predetermined inventory level based on the excess device differential, thereby providing a dynamic and flexible approach to managing the inventory of devices having a finite usable lifetime.

According to a fourth aspect of the present invention, an inventory control system for controlling an inventory of a plurality of point-of-care diagnostic devices comprises means for entering data associated with the devices. The inventory includes a main inventory and at least one subinventory. The plurality of devices includes at least one type of device. Each device is configured to perform at least one sample analysis, and each device has a usable lifetime. The data includes a current number of at least one type of device in the main inventory and a predetermined minimum number of devices of that type in the main inventory, and includes a current number of at least one type of device in the at least one subinventory and a predetermined minimum number of devices of that type in the at least one subinventory, wherein each of the at least one subinventory is associated with a point-of-care location. The inventory control system comprises means for displaying data associated with the devices and means for storing data associated with the devices. The inventory control system also comprises means for automatically updating the current number of devices in the at least one subinventory in response to an occurrence of an event that causes a change in the current number of devices in the at least one subinventory.

According to a fifth aspect of the present invention, an inventory control system for controlling the use of a plurality of point-of-care diagnostic devices in an inventory includes a data input interface for entering data associated with the devices. The data includes an indicator associated with at least one device. The plurality of devices includes at least one type of device, wherein each device is configured to perform at least one sample analysis. The inventory includes a refrigerated inventory and an ambient temperature subinventory. The devices are stored in the refrigerated inventory and transferred to the ambient temperature subinventory prior to use. Each device has an ambient temperature usable lifetime. The inventory control system includes a memory for storing data associated with the devices and for storing steps of a computer program to: (i.) receive an indication from the indicator associated with the at least one device, prior to performing sample analysis using the at least one device; (ii.) determine, using the indication, whether the ambient temperature usable lifetime of the at least one device has been exceeded; and (iii.) prevent the at least one device from being used when a determination is made that the ambient temperature usable lifetime of the at least one device has been exceeded. The inventory control system also includes a processor for accessing the memory to execute the computer program.

According to the fifth aspect, the indicator comprises a code associated with the at least one device. The memory stores steps of a computer program to: receive a first instance of the code associated with the at least one device, when the at least one device is transferred from the refrigerated inventory to the ambient temperature subinventory; and associate a first time indication with the first instance of the code associated with the at least one device. For the step of receiving an indication, the memory stores steps of a computer program to: receive a second instance of the code associated with the at least one device, prior to performing sample analysis using the at least one device; and associate a second time indication with the second instance of the code associated with the at least one device. For the step of determining, the memory stores steps of a computer program to compare the first and second time indications with the ambient temperature usable lifetime of the at least one device. According to another alternative exemplary embodiment, the indicator is a time-temperature indicator.

According to a sixth aspect of the present invention, a method for controlling the use of a plurality of point-of-care diagnostic devices in an inventory comprises the steps of: (i.) entering data associated with the devices, wherein the data includes an indicator associated with at least one device, wherein the plurality of devices includes at least one type of device, wherein each device is configured to perform at least one sample analysis, wherein the inventory includes a refrigerated inventory and an ambient temperature subinventory, wherein the devices are stored in the refrigerated inventory and transferred to the ambient temperature subinventory prior to use, and wherein each device has an ambient temperature usable lifetime; (ii.) receiving an indication from the indicator associated with the at least one device, prior to performing sample analysis using the at least one device; (iii.) determining, using the indication, whether the ambient temperature usable lifetime of the at least one device has been exceeded; and (iv.) preventing the at least one device from being used when a determination is made that the ambient temperature usable lifetime of the at least one device has been exceeded.

According to the sixth aspect, the indicator is a code associated with the at least one device, and the method comprises the steps of: receiving a first instance of the code associated with the at least one device, when the at least one device is transferred from the refrigerated inventory to the ambient temperature subinventory; and associating a first time indication with the first instance of the code associated with the at least one device. The step of receiving an indication comprises the steps of: receiving a second instance of the code associated with the at least one device, prior to performing sample analysis using the at least one device; and associating a second time indication with the second instance of the code associated with the at least one device. The step of determining comprises the step of comparing the first and second time indications with the ambient temperature usable lifetime of the at least one device. According to another alternative exemplary embodiment, the indicator is a time-temperature indicator.

BRIEF DESCRIPTION OF THE DRAWINGS

Other objects and advantages of the present invention will become apparent to those skilled in the art upon reading the following detailed description of preferred embodiments, in conjunction with the accompanying drawings, wherein like reference numerals have been used to designate like elements, and wherein:

FIG. 1 illustrates an exemplary table comparing monthly demand for different devices at various hospital locations.

FIG. 8 is a flow chart illustrating the steps for re-dispatching the point-of-care diagnostic devices between local inventories to reduce excess devices, in accordance with exemplary embodiments of the present invention.

FIG. 9 is a flow chart illustrating steps for locking out point-of-care diagnostic devices, in accordance with an exemplary embodiment of the present invention.

DETAILED DESCRIPTION OF THE PREFERRED EMBODIMENTS

Figure 2:
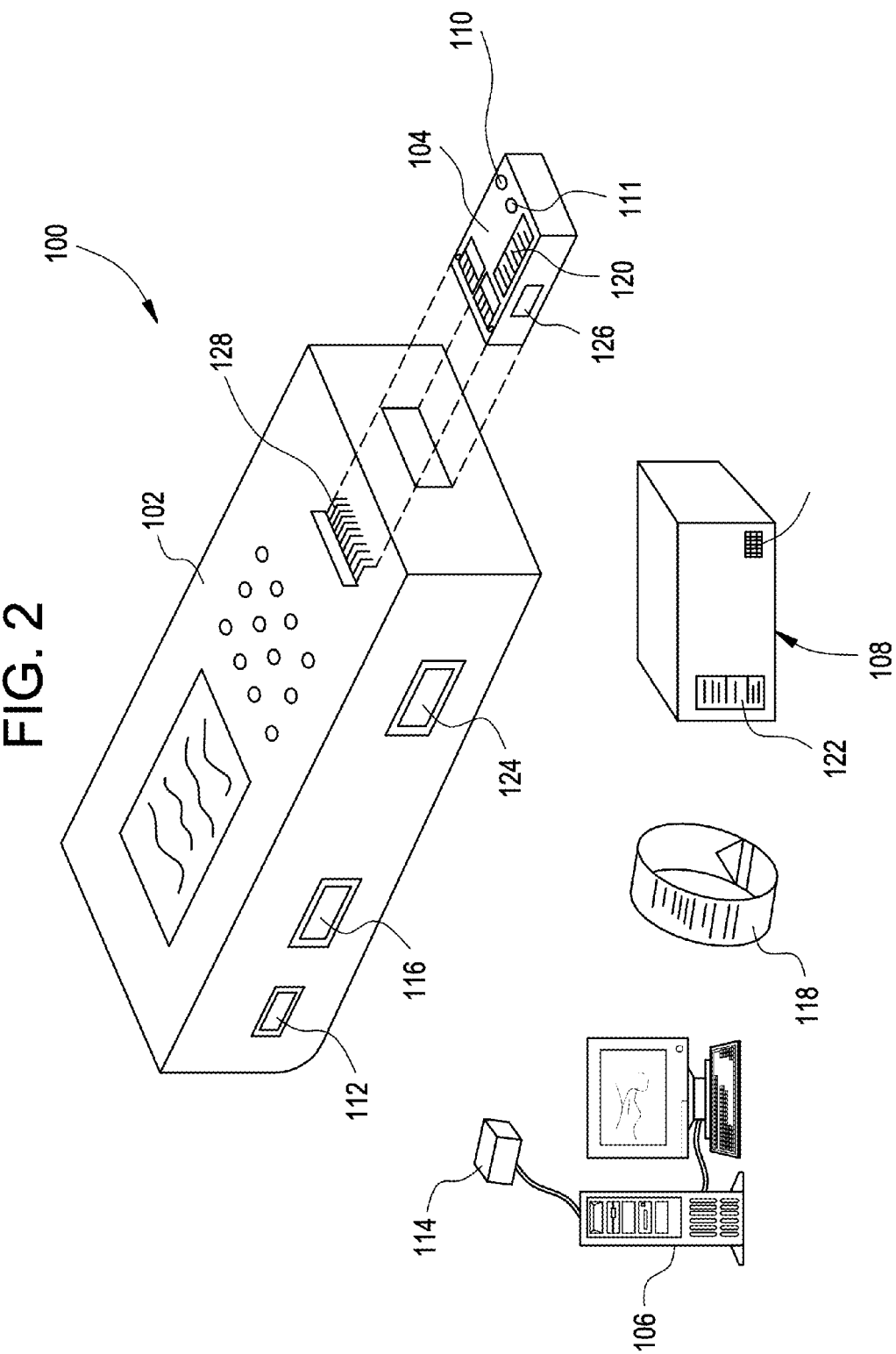
FIG. 2 is a block diagram illustrating an inventory control system for controlling an inventory of a plurality of point-of-care diagnostic devices, in accordance with an exemplary embodiment of the present invention.

A system and method are disclosed for controlling an inventory of a plurality of point-of-care diagnostic devices. The plurality of devices includes at least one type of device. Each device is configured to perform at least one sample analysis, and each device has a usable lifetime. The inventory includes a main inventory and at least one subinventory. Each subinventory is associated with a point-of-care location. The inventory control system comprises a data input interface for entering data associated with the devices and a data output interface for displaying data associated with the devices. The data can include a current number of at least one type of device in the main inventory and a predetermined minimum number of devices of that type in the main inventory, and can include a current number of at least one type of device in the at least one subinventory and a predetermined minimum number of devices of that type in the at least one subinventory. A memory stores data associated with the devices and stores steps of a computer program to automatically update the current number of devices in the at least one subinventory in response to an occurrence of an event that causes a change in the current number of devices in the at least one subinventory. For example, the event can include, but is not limited to, at least one of (i.) a device from the at least one subinventory is used to perform at least one sample analysis, (ii.) a device from the at least one subinventory is transferred to another subinventory, and (iii.) a device from the at least one subinventory exceeds the usable lifetime of the device. However, the event can be any type of event that can cause a change in the current number of devices. The inventory control system also includes a processor for accessing the memory to execute the computer program.

Exemplary embodiments of the present invention provide an automated system that ensures the maintenance of an adequate inventory of different types of disposable devices at multiple locations within a hospital. The disposable diagnostic devices can include, for example, blood analysis devices, urine analysis devices, serum analysis devices, plasma analysis devices, saliva analysis devices, cheek swab analysis devices, or any other type of disposable diagnostic device that can be used for point-of-care sample testing. Other consumable items, that are used in conjunction with the sample testing device or a reading apparatus, can also be inventory items in the automated system, and the system is capable of providing an adequate inventory of those items, as well. These consumable items can include, for example, syringes, vacutainers, swabs, needles, capillary tubes and collection devices, control fluids of different types, printer paper, batteries, and the like. The automated system according to exemplary embodiments is capable of initiating automatic reordering of devices of various types from the supplier, in relation to the consumption of devices at a given institution. The automated system can redistribute devices between locations within a hospital when a temporarily inadequate inventory exists at a central location within a hospital, for instance where there is an emergency medical situation causing a spike in demand for devices in one particular department, or where supplies of new devices to the hospital from the supplier have been delayed by a transportation emergency.

Additionally, where devices have a fixed shelf life, the automated system of the present invention ensures that inventory is supplied from the central inventory to ensure a high remaining shelf life in the central inventory, for example, using a first in, first out (FIFO) mode of operation. The automated system can be controlled by a computer and optionally integrated into an existing laboratory information system and a hospital information system. The automated system of the present invention provides a user-friendly, and optionally substantially real-time, display of inventory levels of each device type at each location where devices are used or stored. Exemplary embodiments of the present invention can also provide a user-friendly tracking means for following the different types of device consumption occurring in a hospital for the purpose of assisting the hospital in the analysis of operations, making forecasts, planning and the like.

Exemplary embodiments of the present invention can control the use of a plurality of point-of-care diagnostic devices in an inventory. Devices can be stored in a refrigerated inventory and transferred to an ambient temperature subinventory prior to use. Each device has an ambient temperature usable lifetime. A device or a collection of devices can be prevented from being used when a determination is made that the ambient temperature usable lifetime of the device or devices has been exceeded. The determination can be made, for example, by using a time-temperature indicator associated with each device that indicates when the ambient temperature usable lifetime of the device has been exceeded. Alternatively, a code, such as, for example, a bar code, RF tag or the like, can be associated with a device or collection of devices. When the device or devices are transferred from the refrigerated inventory to the ambient temperature subinventory, a first timestamp can be associated with the code. Prior to the use of the device or devices, a second timestamp can be associated with the code and can be compared to the first timestamp. The device or devices can be prevented from being used if the time difference between the two timestamps exceeds the ambient temperature usable lifetime of the device or devices.

These and other aspects of the present invention will now be described in greater detail. FIG. 2 is a block diagram illustrating an inventory control system for controlling an inventory of a plurality of point-of-care diagnostic devices, in accordance with an exemplary embodiment of the present invention. The system 100 includes a reading apparatus 102, a disposable device 104, a central data station 106 and a box of devices 108. The reading apparatus 102 can include, for example, a display, electronic memory and a keypad for manual data entry. The disposable device 104 can include, for example, a port for receiving a patient sample 110. The reading apparatus 102 can communicate with the central data station 106 using, for example, a wire, a wireless connection, an infrared link, an optical link, a network connection 112, 114, or any other form of communication link that uses any form of communication protocol to transfer information electronically.

The reading apparatus 102 can include a barcode reader 116 for reading information from a patient's bar-coded wristband 118, from a barcode 120 on a device 104 or from any other item 122 (e.g., the box of devices 108) used in conjunction with the reading apparatus 102. Other such encoding arrangements can be used. For example, the reading apparatus 102 can also include (either alternatively or in addition to the barcode reader 116) a radio-frequency (RF) identification device 124 that is capable of identifying a RF tag 126 that is contained on or in each individual device or each box of devices 108.

According to another exemplary embodiment of the present invention, one or more of the encoding arrangements can be based upon a binary coding pin array 128 of the type disclosed in, for example, jointly-owned U.S. Pat. No. 4,954,087.

The various encoding arrangements can convey relevant information such as, for example, the identity of a specific device type, date and location of manufacture, manufacturing lot number, expiration date, a unique number associated with a device, coefficients for use by the reading apparatus 102 associated with the calculation of blood or other sample parameters and the like. The devices can be used for measurements selected from groups such as, for example, amperometric, potentiometric, conductimetric, optical and the like. Other relevant information of this general type is well known in the medical manufacturing art, as is the technology for bar coding and barcode recognition.

For encoding on the basis of radio-frequency (RF) communication, the device 104 can include a tag on which one or more indications of, for example, the refrigerator shelf life of the device 104, the ambient temperature shelf life of the device 104, the age of the device 104, and the like is located. Alternatively, rather than including numerous elements of relevant information on the tag, a single piece of information, e.g., a lot number, can be included on the tag. The lot number can be any alphanumeric sequence or unique identifier that can be used to identify the device 104 and associate relevant information with that device. For example, the lot number can be applied to a lookup table or any other type of computer database located within or connected to the reading apparatus 102 or any other computing system. Using the lookup table or computer database, relevant shelf life or other such information can be associated with the lot number such that, based on the lot number, the refrigerator shelf life, the ambient temperature shelf life, the age of the device 104 and the like can be determined.

The technology for RF encoding and RF code recognition using RF identification coded tags are known to those skilled in the art. A RF identification device 124, 126 can comprise, for example, a self-contained, passively powered device with, for example, an antenna, memory, transmitter and the like in a package with dimensions of, for example, a few millimeters. The RF identification device 124 can be implemented on, for example, a printed circuit board with a serial port with dimensions of, for example, about one square centimeter or more. Alternatively, the RF identification device 124 can be in the form of, for example, an application specific integrated circuit (ASIC) for integration into an established system. However, the RF identification device 124 can be implemented using hardware, firmware, or any combination thereof, with the size of the device dependent upon the means of implementation. The electronic components for RF encoding can be selected to determine the proximity of the encoding element to the receiving component for reliable transmission to occur. Such proximity can range from, for example, a few millimeters up to a few meters, although the actual proximity will depend upon the choice of electronic components. Optionally, the proximity can be set such that the exchange of information occurs when the device 104 is inserted into the reading apparatus 102.

The aforementioned encoding arrangements differ in the amount of information that can be conveniently transferred to the reading apparatus 102 and the required proximity between the reading apparatus 102 and source of the information. For the binary pin array of U.S. Pat. No. 4,954,087, there is physical contact between the device 104 and the reading apparatus 102 and the data is limited by the number of available pins, generally in the range of, for example, two to about twenty pins. For bar-coding, the user brings the barcode and reading apparatus 102 into close proximity and at a specific orientation relative to each other. However, the data contained in the barcode can be significantly greater than the binary pin array. The RF encoding approach offers even greater data capabilities without requiring the user to bring the device 104 into a specific orientation with the reading apparatus 102 for successful transmission.

The devices 104 can have a finite refrigerator and ambient temperature shelf life. For example, the devices 104 can have a refrigerated usable lifetime in the range of, for example, about three months to three years, although the devices 104 could have any range of refrigerated usable lifetime. The devices 104 can have an ambient temperature usable lifetime in the range of, for example, about three days to three months, although the devices 104 can have any range of ambient temperature usable lifetime. Given that the devices 104 can have a finite refrigerator and ambient temperature shelf life, there is a need to ensure that expired devices 104 (i.e., the devices 104 that have exceeded the refrigerated or ambient temperature shelf life) are not used.

In accordance with exemplary embodiments, the device 104 can include an indicator 111, such as, for example, a time-temperature indicator, that provides an indication of whether the device 104 has expired. For indicator 111, the device 104 can include temperature-sensing circuitry (e.g., hardware, firmware, or any combination thereof) for monitoring the temperature of the device 104. When the temperature-sensing circuitry included in device 104 determines that the temperature of the device 104 has remained within a certain range (e.g., ambient temperature) for a period of time that is greater than a predetermined threshold (e.g., the ambient temperature shelf life), the circuitry can provide an electrical signal to indicator 111 that causes the indicator 111 to emit an indication (e.g., a flashing, blinking or steady light, a change in color, a sound, and the like) that the device 104 is expired. Alternatively, the temperature monitoring component can be based on a physical or chemical change that is temperature dependant. This can result in, for example, a physical or color change that is registered by the reading apparatus 102. The temperature monitoring component can be, for example, a liquid crystal or mechanical device, for example, a threshold device with a wax seal that, when melted at a certain temperature, releases a spring, or any other type of liquid crystal or mechanical device that is temperature sensitive and can register or otherwise indicate that the device 104 has expired based on temperature.

The temperature monitoring component can alternatively be a device that acts as a time-temperature monitor with a threshold that equates to a safe, but variable, lifetime. In other words, the time-temperature monitor can either increase or decrease the lifetime of the device 104 depending upon the temperature in which the device 104 is kept. For example, a device 104 that has been removed from a refrigerator and has been maintained at a low ambient temperature (e.g., at or near the refrigerator temperature), for example, a military MASH unit during a winter deployment, can have a time-temperature indicator that permits, for example, one extra week of post-refrigerator shelf-life because of the low ambient temperature. Alternatively, the same MASH unit in a desert deployment in which the ambient temperature is high (e.g., well above the refrigerator temperature), can have a time-temperature indicator that expires before one where the ambient temperature is lower. However, those of ordinary skill in the art will recognize that the amount of increase or decrease in the lifetime of the device 104 will depend upon the actual ambient temperature of the post-refrigerator environment into which the device 104 is removed, and will thus vary accordingly. As used herein, "refrigerated storage" generally refers to storage in the range of about 36 to about 46 degrees Fahrenheit (about 2 to about 8 degrees Celsius), and "room temperature storage" generally refers to storage in the range of about 64 to about 86 degrees Fahrenheit (about 18 to about 30 degrees Celsius). Ambient storage conditions can be similar to room temperature storage, but can be in the range of about 36 to about 104 degrees Fahrenheit (about 2 to about 40 degrees Celsius).

According to an alternative exemplary embodiment of the present invention, the device 104 or a collection of devices 104 (e.g., a box of devices 108) can be prevented from being used by comparing, for example, time indicators associated with the device 104 with the ambient temperature usable lifetime of the device or devices 104. For example, each device or devices 104 can have a code, such as for example, a bar code, RF tag or the like, associated with the device or devices 104. When the device or devices 104 are transferred from a refrigerated inventory to an ambient temperature sub-inventory, a first instance of the code associated with the device or devices 104 can be entered into the reading apparatus 102 via the identification device associated with the reading apparatus 102 (e.g., via barcode reader 116 or the like). A first time indication, such as, for example, a first timestamp, can be associated with this first instance of the code by the reading apparatus 102. Prior to performing sample analysis using the device or devices 104, a second instance of the code associated with the device or devices 104 can be entered into the reading apparatus 102 via the identification device associated with the reading apparatus 102. A second time indication, such as, for example, a second timestamp, can be associated with the second instance of the code by the reading apparatus 102. The time difference between the two timestamps can then be determined, and this time difference can be compared to the ambient temperature usable lifetime of the device or devices 104. If the time difference exceeds the ambient temperature usable lifetime of the device or devices 104, the device or devices 104 can be prevented from being used. For example, the operator can be notified that the device or devices 104 have expired through visual means (e.g., a warning message is displayed on the display of the reading apparatus 102, an warning light or indicator blinks or otherwise flashes on the reading apparatus 102, or the like), audible means (e.g., a warning sound is played by the reading apparatus 102), an electronic message relayed to the operator, central repository, or other entities through a computer or other network connection, or the like.

Referring to the disposable device 104 and the patient sample entry port 110, the device 104 can perform analyses on a range of sample types. These sample types can include, for example, arterial, capillary and venous blood, plasma, serum, interstitial and spinal fluid, urine, bodily secretions and the like. Appropriate consumable items for use in conjunction with the device 104 are well known in the art. These include, for example, vacutainers, needles, capillary tubes and collection devices, control fluids of different types, syringes, swabs, printer paper, batteries and any other consumable item that can be used in conjunction with the device 104. The consumable items can also be used to facilitate introduction of the sample into the sample entry port 110.

Figure 3:
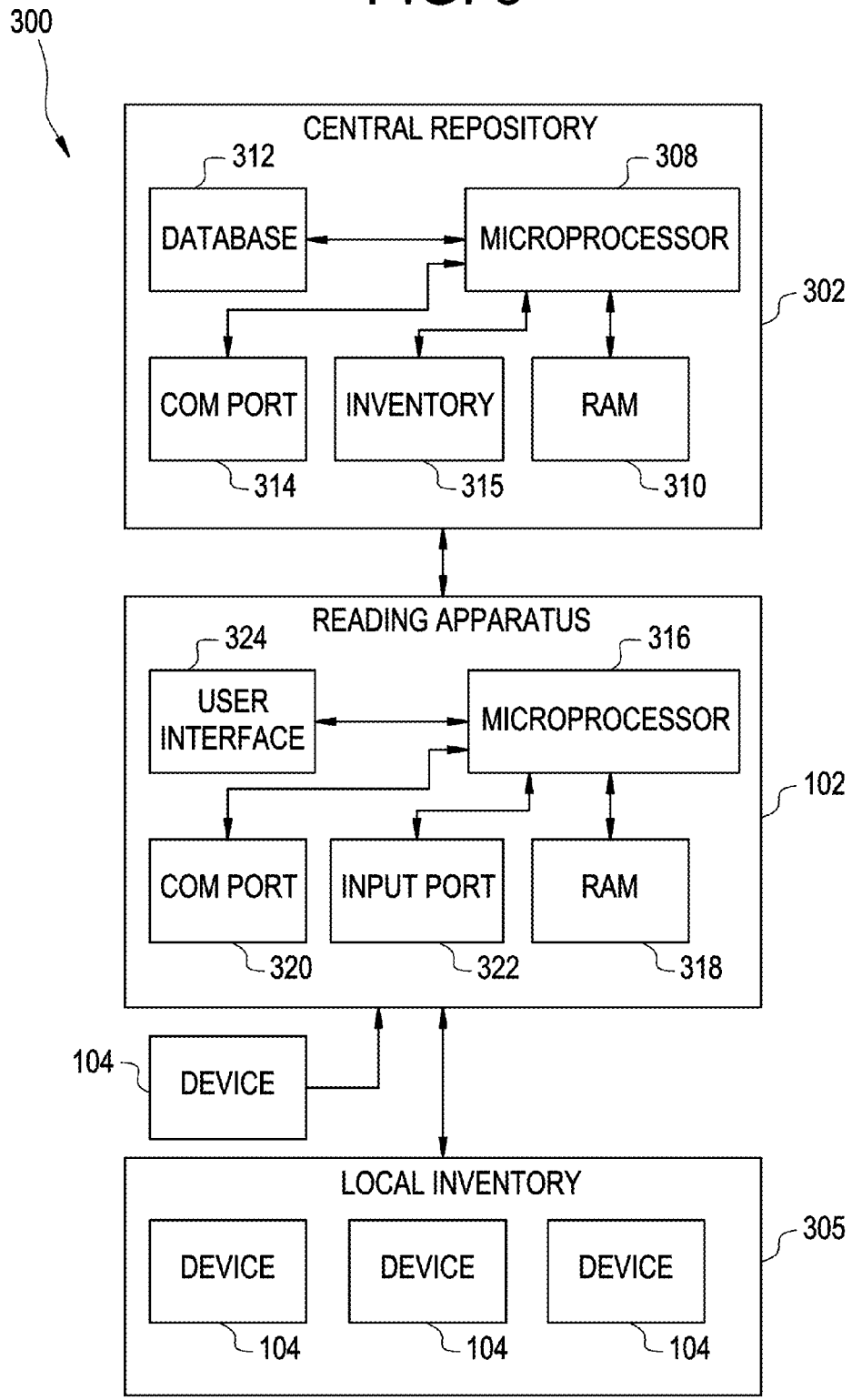
FIG. 3 is a block diagram illustrating an inventory control system for controlling an inventory of a plurality of point-of-care diagnostic devices, in accordance with an exemplary embodiment of the present invention.

FIG. 3 is a block diagram illustrating an inventory control system for controlling an inventory of a plurality of point-of-care diagnostic devices, in accordance with an exemplary embodiment of the present invention. The system 300 can include a central repository 302, a reading apparatus 102, a local inventory of devices 305, and a device 104. The central repository 302 can include a microprocessor 308. The microprocessor 308 can be any type of processor, such as, for example, any type of general purpose microprocessor or microcontroller, a digital signal processing (DSP) processor, an application-specific integrated circuit (ASIC), a programmable read-only memory (PROM), an erasable programmable read-only memory (EPROM), an electrically-erasable programmable read-only memory (EEPROM), a computer-readable medium, or the like.

The central repository 302 can also include computer memory, such as, for example, RAM 310. However, the computer memory of central repository 302 can be any type of computer memory or any other type of electronic storage medium that is located either internally or externally to the central repository 302, such as, for example, read-only memory (ROM), random access memory (RAM), compact disc read-only memory (CDROM), electro-optical memory, magneto-optical memory, or the like. According to exemplary embodiments, RAM 310 can contain, for example, the operating program for the central repository 308. As will be appreciated based on the following description, the RAM 310 can, for example, be programmed using conventional techniques known to those having ordinary skill in the art of computer programming. The actual source code or object code for carrying out the steps of, for example, a computer program can be stored in the RAM 310.

The central repository 308 can also include a database 312. The database 312 can be any type of computer database for storing, maintaining, and allowing access to electronic information stored therein. For example, the database 312 can contain information relating to threshold requirements of the device 104 for each reading apparatus 102, e.g., the minimum desired number of devices 104 to be maintained in local inventory 305. The central repository 308 can also include a communications port 314 with which the central repository 302 can communicate with the reading apparatus 102. The communications port 314 can be any type of communications port through which electronic information can be communicated over a communications connection, whether locally or remotely, such as, for example, an Ethernet port, an RS-232 port, or the like. The central repository 302 can also include an inventory 315, which can be a physical repository of devices 104, other consumable items that can be used in conjunction with the devices 104, or the like.

The reading apparatus 102 can include a microprocessor 316 (e.g., any type of processor). The reading apparatus can also include any type of computer memory or any other type of electronic storage medium that is located either internally or externally to the reading apparatus 102, such as, for example, RAM 318. According to exemplary embodiments, the RAM 318 can contain, for example, the operating program for the reading apparatus 102. As will be appreciated based on the following description, the RAM 318 can, for example, be programmed using conventional techniques known to those having ordinary skill in the art of computer programming. The actual source code or object code for carrying out the steps of, for example, a computer program can be stored in the RAM 318.

The reading apparatus 102 can include a communications port 320 (e.g., any type of communications port through which electronic information can be communicated over a communications connection, whether locally or remotely) with which the reading apparatus 102 can communicate with, for example, the central repository 302. The reading apparatus 102 can also include an input port 322 that, for example, allows insertion of the device 104 and is appropriately configured to receive the device 104. The reading apparatus 102 can also include a user interface 324. The user interface 324 can be any type of computer monitor or display device on which graphical and/or textual information can be displayed to a user (e.g., through a graphical user interface) and which allows a user to enter information (e.g., commands and the like) through, for example, a keyboard, a touch-screen, any type of pointing device, electronic pen, and the like. For example, the user interface 324 can be configured to receive instructions from the operator of the reading apparatus 102.

According to exemplary embodiments, the local inventory 305 is a repository of physical items that can include, for example, the actual devices 104 of one or more types of devices that are available to the reading apparatus 102. However, the local inventory 305 can also include any other consumable item that can be used in conjunction with the devices 104.

According to an exemplary embodiment, the number of devices 104 that are associated with the local inventory 305 can be entered electronically, for example, through a scanning arrangement using a barcode reader, data transmission from the central repository 302, or other electronic means. According to an alternative exemplary embodiment, the number of devices 104 can be entered manually. The initial stock level can be set through, for example, an electronic notification, manual entry, application summing notifications, and the like. With respect to an electronic notification, the initial stock level can be set electronically by, for example, a message from the supplier with an indication of the quantity and type of devices 104. With respect to application summing notifications, when inputting the initial stock level, the number of devices 104 in each box 108 can be allocated based on a single scan of the box. For example, where each box 108 of devices 104 can have a barcode 122 (see FIG. 2) that identifies the type of the devices 104 and number of devices 104 in the box 108, the user can swipe the box 108 past the barcode reader 116 located on the reading apparatus 102. The number of devices 104 in the box 108 may be in the range of, for example, 1 to 100. However, it should be appreciated that the number of devices 104 in the box 108 can vary, for example, with the size of the box 108. Alternatively, the barcode reader 116 can be located on a departmental central data station (CDS). If multiple boxes 108 of the same device 104 type are being added to the department's local inventory 305, then the user can swipe all the boxes, swipe the first box and manually input the total number of boxes, or some combination in between. It should be appreciated by persons of ordinary skill in the art that application summing notifications can be manual or automatic, based on, for example, electronic notifications, as described above.

Alternatively, when the devices 104 arrive at a given department from the central repository 302, the boxes 108 can be scanned by, for example, bar-code or RF means, thereby updating the departmental local inventory 305. The inventory information can be recorded in the CDS and a message can be optionally sent back to the central repository 302 confirming that the correct devices 104 have arrived. The central repository 302, or a second location, can be, for example, a hospital central laboratory store, or a general hospital store. In some circumstances where the hospital is small, or there are supply constraints, the central repository 302 can be off-site, such as, for example, a hospital supply company store or a device 104 and consumables store at a remote vendor location.

Figure 4:
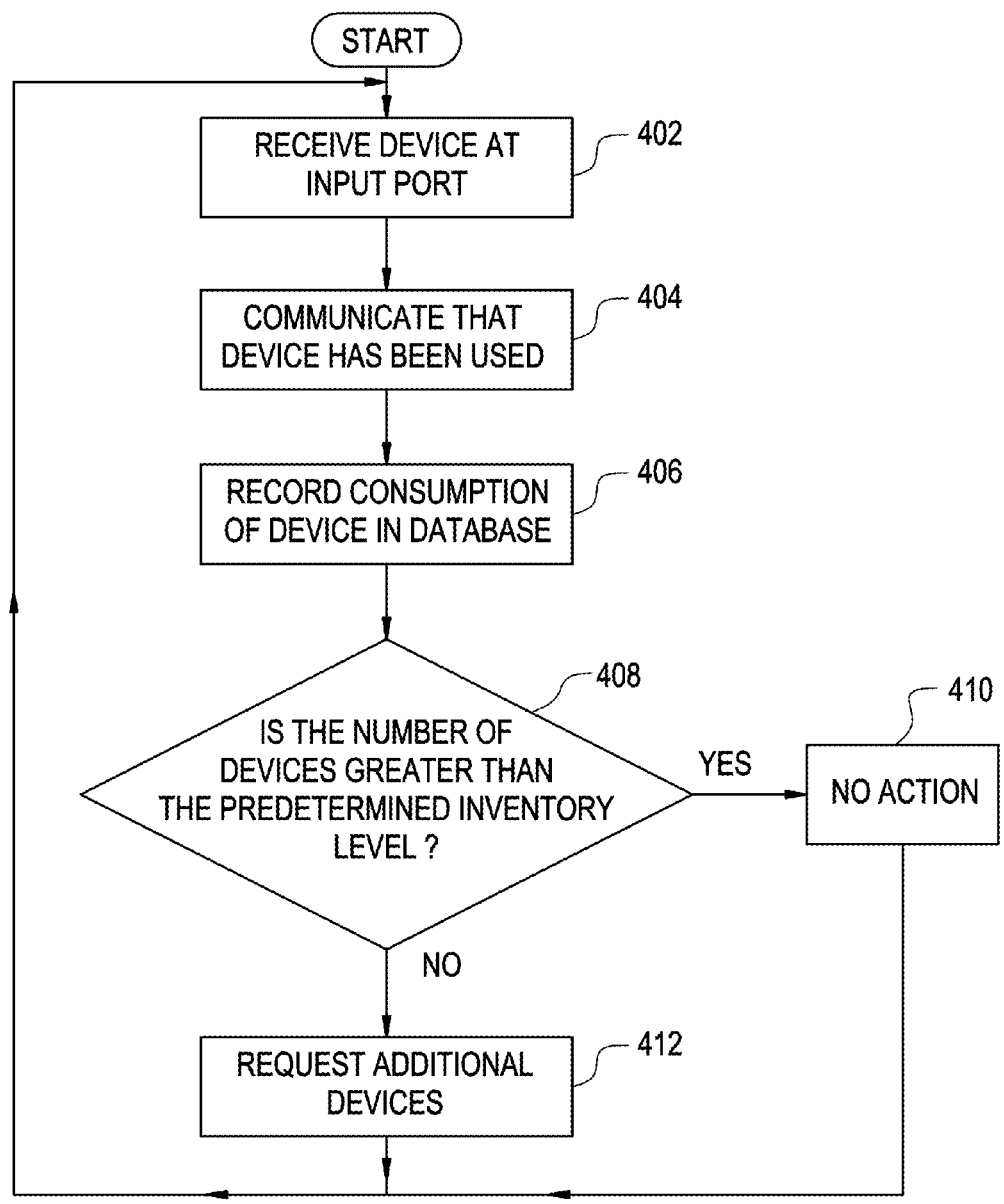
FIG. 4 is a flow chart illustrating the steps for maintaining an adequate supply of point-of-care diagnostic devices, in accordance with an exemplary embodiment of the present invention.

When a device 104 is consumed by the reading apparatus 102, it is desirable to maintain an adequate supply of devices 104 available for further consumption by the reading apparatus 102. FIG. 4 is a flow chart illustrating the steps for operating the system 300 to maintain an adequate supply of devices 104, in accordance with an exemplary embodiment of the present invention. First, the reading apparatus 102 receives the device 104 at the input port 322 (block 402). The device 104 can be received by any of the arrangements that have been described, including physical interface, barcoding, RF interface, infrared interface, and the like. Upon receipt of the device 104, the reading apparatus 102 can communicate via COM port 320 to the central repository 302 that the device 104 has been used (block 404). The central repository 302 can record the consumption of device 104 in the database 312 (block 406). The central repository 302 can compare the number of devices 104 that are available in local inventory 305 to the reading apparatus 102 with a predetermined minimum inventory level for the reading apparatus 102 (block 408). Based on, for example, the consumption rate for a device at a given point-of-care location, the predetermined minimum inventory level for that location can be set. For purposes of illustration and not limitation, if the ambient shelf-life of the device is two weeks, the predetermined minimum inventory level can be set to one week. However, those of ordinary skill in the art will recognize that the predetermined minimum inventory level can be set based on any one or combination of additional or alternative factors that are associated with the given point-of-care location, such as, for example, a location's needs, device usage rate, the rate at which devices are wasted, the rate at which devices are transferred to other locations, and the like.

If it is determined that the number of devices 104 that are available to the reading apparatus 102 is above the predetermined minimum inventory level, then no action is required (block 410). If it is determined that the number of devices 104 that are available to the reading apparatus 102 is below the predetermined minimum inventory level, then the central repository 302 can request that additional devices 104 be dispatched so that they can be made available to the reading apparatus 102 (block 412). The additional devices 104 can be dispatched from within the hospital or from outside of the hospital. It may be desirable, as a matter of economy, that a first in, first out (FIFO) method be adopted, as this preserves the devices 104 with the longest remaining refrigerated shelf-life in the central repository 302. Thus, according to exemplary embodiments, the consumption of devices 104 by the reading apparatus 102 can be monitored to ensure an adequate supply of devices 104 for each reading apparatus 102.

According to an exemplary embodiment of the present invention, a unique identification code can be associated with each reading apparatus 102. The unique identification code can be contained in each communication to the central repository 302. The central repository 302 can contain information in its database 312 that allows the central repository 302 to identify the location of a specific reading apparatus 102. For example, the central repository 302 can recognize, based on identifying information (e.g., Internet Protocol (IP) address) contained within the database 312, the specific infrared link, network port, or other communication connection that is used by the reading apparatus 102, thereby identifying the location of the reading apparatus 102. Thus, the central repository 302 can track the inventory levels in each department's local inventory 305. When devices 104 are dispatched to a given department, one or more of the reading apparatus 102 in that department can be used to scan the new inventory.

According to exemplary embodiments of the present invention, initiation of the dispatch of the devices 104 and other consumable items from the central repository 302 to the individual departments can be prompted by sending an instruction for dispatch by a hospital's consumables management system. This can be, for example, an e-mail communication to personnel in the central repository 302, an automated dispatch instruction where inventory management at the central repository 302 is automated and under computer control, a display message on the computer screen of the management system, or any other form of communication of an instruction typical of a hospital's consumables management system. It will be apparent to one skilled in the art that the degree of automation and computer control will vary between these institutions. Thus, the exact embodiment of the dispatch initiation is dependent upon the needs, budget, existing management system infrastructure, and the like of the hospital.

According to exemplary embodiments, the central depository 302 determines whether the number of devices 104 in local inventory 305 is adequate for reading apparatus 102. However, it should be appreciated that such a determination can be made by other computing systems, such as by reading apparatus 102. It should also be appreciated that, while a single reading apparatus 102 is shown in FIG. 3, multiple reading apparatus 102 can be included within the system 300, and specifically within a department sharing the local inventory 305 within the hospital. According to exemplary embodiments, the number of devices 104 that are available in the local inventory 305 for use by any of the reading apparatus 102 is monitored so that an adequate supply of devices 104 are available for use with each of the reading apparatus 102.

It should further be appreciated by persons of ordinary skill in the art that the method of FIG. 4 is applicable to a variety of types of devices 104, each of which is capable of being used for a different test. The devices 104 can include, for example, blood analysis devices, urine analysis devices, serum analysis devices, plasma analysis devices, saliva analysis devices, cheek swab analysis devices, or any other type of disposable diagnostic device that can be used for point-of-care sample testing. The central repository 302 can monitor the use of particular types of devices 104 and can dispatch further inventories of those particular devices 104. The method of FIG. 4 is also applicable to other types of consumable items as herein described. For example, in a neonatal intensive care unit (NICU), each device 104 may be used with a heel-stick device, a capillary collection device, a swab to clean the collection site, a pair of latex gloves, and the like. In an emergency room, a device 104 for electrolytes may be used in conjunction with a swab, latex gloves, a needle-stick device, a vacutainer, a syringe, and the like. Other combinations of consumable items would be evident to those performing point-of-care testing. The inventory for the consumable items can thus be effectively monitored according to exemplary methods of the present invention. For example, when dispatching a given number of devices 104 to the NICU, the system can also dispatch a given number of heel-stick devices. Such a determination can be based on, for example, a simple one-to-one relationship or a more complicated algorithmic function that accounts for wastage or alternative uses for the consumable item. For example, an algorithm can be created for the inventory control system by tracking the utilization history of these consumable items versus a device 104.

It should further be appreciated by persons of ordinary skill in the art that the local inventory 305 can contain devices 104 that are refrigerated and that are maintained at ambient temperature. The devices 104 can be identified as being refrigerated or ambient temperature devices (e.g., using their associated identifying information) so that the central repository 302 can maintain proper inventory control of each type of device 104.

Once the local inventory 305 has been inputted into the database 312 (FIG. 3), the system 300 can provide a real-time or near real-time estimate of remaining inventory in the local inventory 305, based on recognizing a consumption of a device 104 or consumable item by receiving an electronic notification from the reading apparatus 102 of the consumption, as described with reference to FIG. 4. While effectively instantaneous communication and real-time estimates are desirable, the high degree of portability of certain types of point-of-care reading apparatus 102 means that the reading apparatus 102 may be temporarily left at a location in which communication is not enabled. Furthermore, the reading apparatus 102 can run several devices 104 while at a location. Accordingly, the RAM 318 or other computer memory of reading apparatus 102 is of sufficient size to allow storage of the device 104 results until a time that the use can be communicated. According to an exemplary embodiment, the RAM 318 can accommodate up to 100 sets of results, although any number of sets of results can be stored in RAM 318, depending on the amount of memory used. Thus, exemplary embodiments of the present invention provide for real-time updates to inventory usage, as well as allow the storage of the usage information in the reading apparatus 102 until such time that this information can be communicated or otherwise downloaded to, for example, the central repository 302.

The system 300 can also provide an on-demand estimate of remaining inventory, based on analyzing data that has been compiled into the database 312. These results can be displayed, for example, on the central data station, at the LIS, at the central repository 102 and on the user interface 324 of each individual reading apparatus 102. The results display can also include a visual or audible flag or warning when estimated inventory falls to, near or below a minimum defined, or predetermined, level. The predetermined level can be set by individual departments or centrally within a hospital to provide for a more efficient overall inventory control based on economic and clinical considerations. These considerations are known in hospital management.

Figure 5:
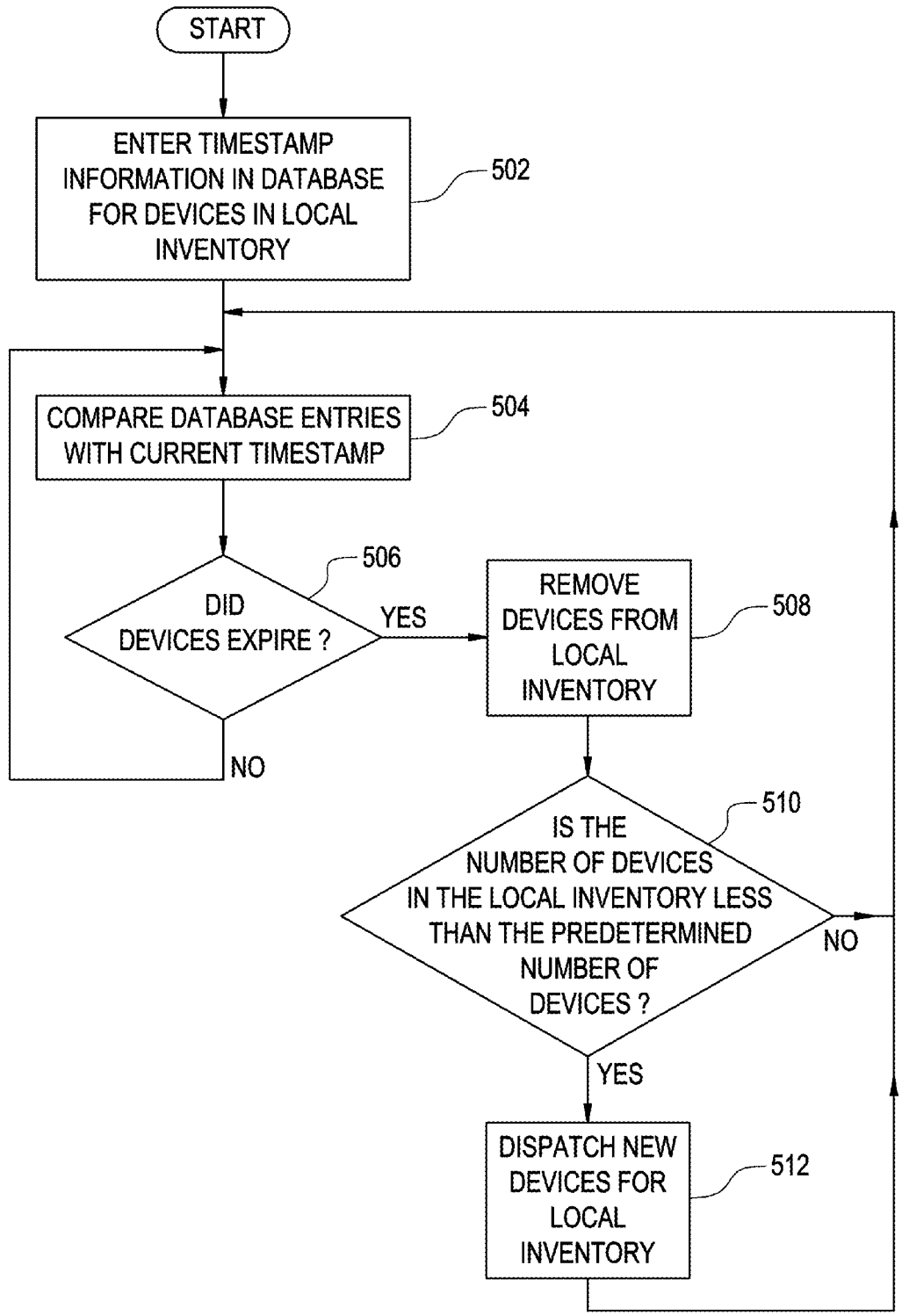
FIG. 5 is a flow chart illustrating the steps for monitoring the shelf-life of point-of-care diagnostic devices and replenishing a local inventory, in accordance with an exemplary embodiment of the present invention.

As was discussed previously, the devices 104 can have a finite shelf-life. Accordingly, it is desirable to maintain an adequate supply of devices 104 that have remaining shelf-life and replenish the local inventory 305 as the shelf-life of the devices 104 expire. FIG. 5 is a flow chart illustrating the steps for monitoring the shelf-life of devices 104 and replenishing the local inventory 305, in accordance with an exemplary embodiment of the present invention. Initially, timestamp information can be entered into the database 312 for the devices 104 that are associated with the local inventory 305 (block 502). The timestamp information can be entered either manually by an operator or electronically, for example, through bar-code reading at the time the devices 104 are entered into the local inventory 305 and communicated to the central repository 302. The timestamp information can be maintained in the database 312 of the central repository 302. The timestamp information can indicate when the devices 104 were added to the local inventory 305 (i.e., creation date) or when the shelf-life of the devices 104 will expire (i.e., expiration date). The central repository 302 can compare the timestamp database entries with the current timestamp (i.e., the current time) (block 504). If it is determined that the devices 104 have not expired (block 506), i.e., the current timestamp is before the expiration date of the devices 104, then the central repository 302 can continue to monitor the timestamp database entries and control is returned to step 504. If it is determined that the devices 104 have expired (block 506), i.e., the current timestamp is after the expiration date of the devices 104, then the devices 104 can be removed from the local inventory 305 (block 508), both physically and from the computer record of their inventory.

It is then determined if the number of devices 104 in the local inventory 305, after the expired devices 104 have been removed, is less than the predetermined number of devices 104 for the local inventory 305 (block 510). If it is determined that the number of devices 104 in the local inventory 305 is above the predetermined number of devices 104, then control is returned to step 504. If it is determined that the number of devices 104 in the local inventory 305 is below the predetermined number of devices 104, then the central repository 302 can dispatch additional devices 104 to replenish the local inventory 305 so that the number of devices 104 exceeds the predetermined minimum number of devices 104 (block 512). Control is then returned to step 504, where the monitoring of the timestamp database entries continues. To provide for economically-efficient consumption of the devices 104, the local inventories 305 can be set to an adequate level to meet demand, but also at a level in which the number of devices 104 that reach their expiration date is reduced or minimized. The number of devices 104 contained within the local inventories 305 can be monitored based on usage so as to dynamically reallocate the number of devices 104 among the local inventories 305 based on trends in usage.

Figure 6:
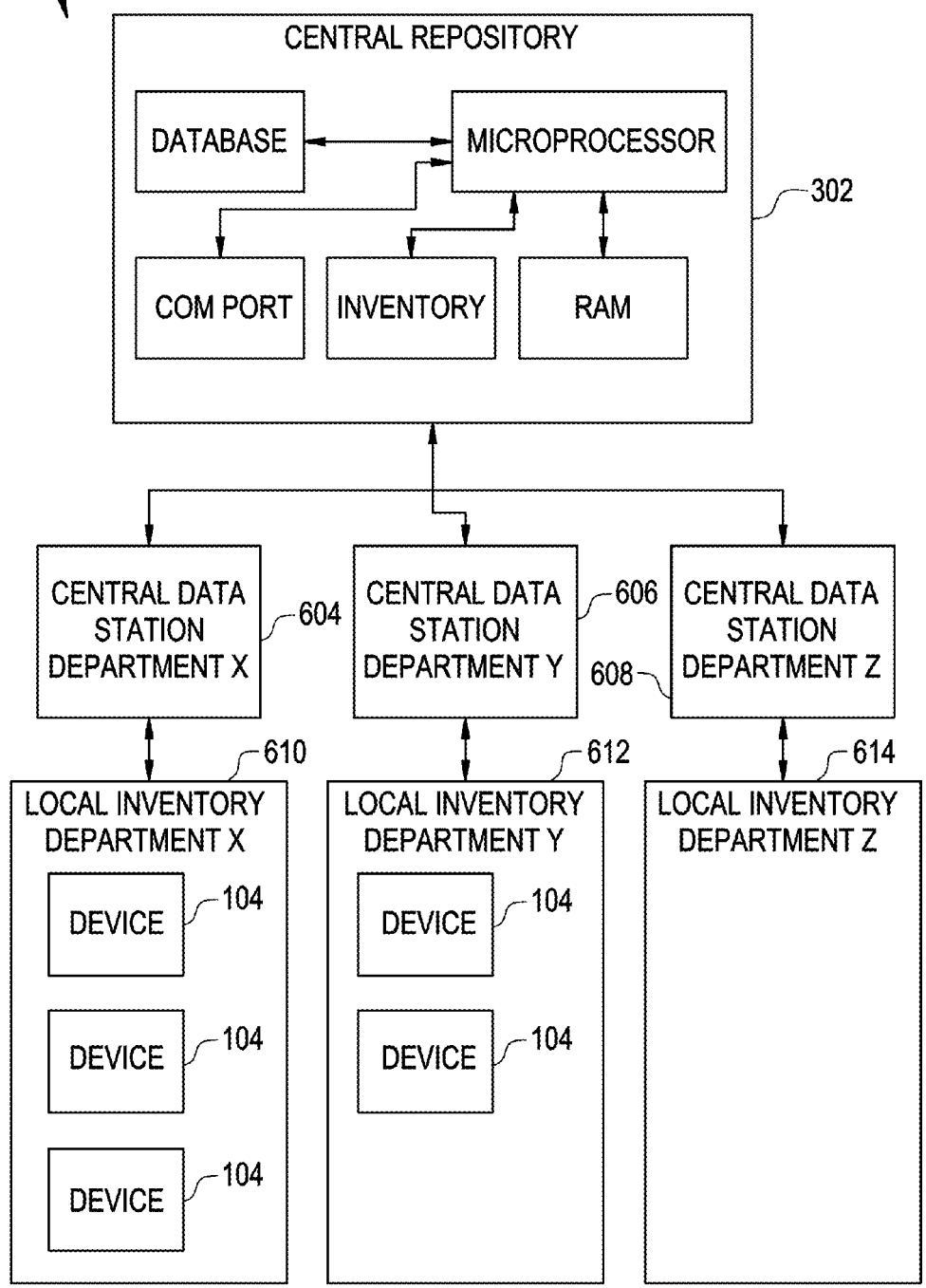
FIG. 6 is a block diagram illustrating a system, including multiple central data stations, wherein the point-of-care diagnostic devices are distributed between departments that are controlled by the central data stations, in accordance with exemplary embodiments of the present invention.

As discussed previously, FIG. 4 illustrates how the devices 104 are dispatched to the local inventory 305 from the central repository 302. FIG. 6 is a block diagram illustrating a system 600, including multiple central data stations 604, 606 and 608, wherein the devices 104 are distributed between the departments that are controlled by the central data stations 604, 606 and 608, in accordance with exemplary embodiments of the present invention. The system 600 includes a central repository 302, a central data station 604 for department X, a central data station 606 for department Y and a central data station 608 for department Z. However, the system 600 can include any number of central data stations. A local inventory 610 is associated with central data station 604, a local inventory 612 is associated with central data station 606 and a local inventory 614 is associated with central data station 606, although any number of local inventories can be associated with each central data station. Local inventories 610, 612 and 614 can contain any number of devices 104. For purposes of illustration and not limitation, in the system 600 depicted in FIG. 6, local inventory 610 includes three devices 104, local inventory 612 includes two devices 104, and local inventory 614 does not include any devices 104.

The central data stations 604, 606 and 608 can provide connectivity between individual reading apparatus 102 and central locations, such as, for example, a LIS or HIS, and device 104 and central repositories 302. The central data stations 604, 606, and 608 can be connected with the various system constituents using any type of communications connection that is capable of transmitting and receiving electronic information, such as, for example, an Ethernet connection or other computer network connection. The central data stations 604, 606 and 608 can optionally provide a direct link back to a vendor's information system, for example via the Internet, a dial-up connection or other direct or indirect communication link, or through the LIS, HIS, or central repository 302. Such an exemplary embodiment can provide for automated re-ordering of devices 104 to maintain the predetermined levels of inventory at the hospital's central repository 302, and allow the vendor to forecast demand and adequately plan the manufacture of the devices 104.

In an emergency situation, the inventory level at the central repository 302 or individual locations can fall below that necessary to meet the normal demand based on the predetermined levels for each department. Thus, the system according to exemplary embodiments of the present invention can automatically adjust the predetermined inventory levels in each department based on various criteria. One exemplary criterion would be, for example, to distribute devices 104 preferentially to the departments that treat patients with highest acuity. Other similar such criteria can be used.

In certain emergency circumstances, the system 600 can initiate transfer of devices 104 from one department or local inventory to another, despite these devices 104 having already been moved out of the central repository 302. For example, where a hospital ER is dealing with a major accident, the devices 104 useful for the triage of patients can be redistributed to the emergency room. In such a situation, a flagged message can be sent from the central repository 302 to the central data stations of departments other than the ER to initiate re-dispatch. The method of redistribution of devices 104 can also be extended to other consumable items used in connection with the devices 104, such that the consumable items can be transferred between departments when necessity arises. Such redistribution of inventory enables the hospital to manage these resources in an efficient manner.

Figure 7:
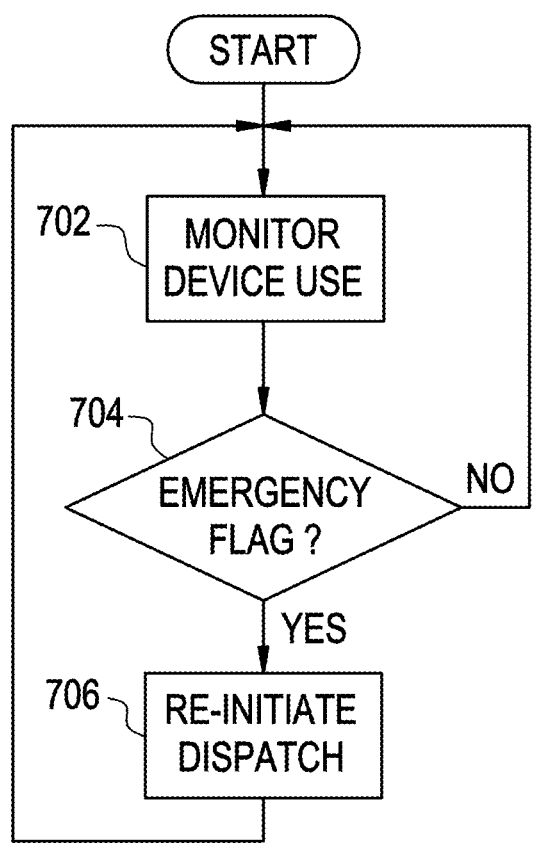
FIG. 7 is a flow chart illustrating steps for determining whether to initiate point-of-care diagnostic device re-dispatch, in accordance with an exemplary embodiment of the present invention.

FIG. 7 is a flow chart illustrating the steps for determining whether to re-dispatch devices 104, in accordance with an exemplary embodiment of the present invention. The central repository 302 can monitor device 104 use and/or expiration (block 702). Thus, the central repository 302 attempts to maintain the local inventory levels above the predetermined inventory level. The central repository 302 can receive messages from, for example, central data stations 604, 606 and 608. If a message is received, the central repository 302 can determine if the message contains an emergency flag (block 704). If the message does not contain an emergency flag, the control returns to block 702. If the message does contain an emergency flag, then the central repository 302 initiates a re-dispatch from amongst the local inventories (block 706), thus maintaining the local inventory level above the predetermined inventory levels.

According to another exemplary embodiment of the present invention, the central repository 302 can be used to control and dynamically modify the predetermined level of inventories 610, 612 and 614 for each department. The central repository 302 can be in direct or indirect communication with a vendor information system (not shown), in which the vendor information system is responsible for providing devices 104 and, optionally, other consumables to the hospital. The central repository 302 can be connected to the vendor information system through human intervention, i.e., verbal communication, but preferably is connected via automated computer-controlled processes, such as, for example, a computer connection (e.g., a dial-up connection, an Internet or other direct or indirect network connection using hard-wired, infrared, optical, wireless or any other form of communication medium that allows for the transfer of electronic information).

The initial predetermined levels of inventory and subsequent modifications can be based on variations in demand between department, the acuity of the patients in the departments, or even an emergency situation, such as, for example, a hospital power failure emergency, a transportation emergency affecting the supply of devices 104 to the hospital, and the like.

Because devices 104 expire within a time period after being placed in an ambient temperature setting, it is desirable to maintain the predetermined inventory level based on actual usage. For example, if a department is not using its allocated devices 104 within the ambient or room temperature storage period, then remaining devices 104 will be wasted. FIG. 8 is a flow chart illustrating the steps for re-dispatching the devices 104 between local inventories 610 to reduce excess devices 104, in accordance with exemplary embodiments of the present invention. The device 104 usage rate is monitored (block 802). The monitoring can be performed by the central repository 302, the reading apparatus 102, or any other computing system. Based on the monitored device 104 usage rate, it can be determined whether any devices 104 will expire, i.e., will not be used before the room temperature or ambient storage time has elapsed (block 804). If devices 104 will not expire, then the device 104 usage rate is again monitored, and control returns to block 802. If devices 104 will expire, then the predetermined inventory level for the department can be lowered to reflect a level that is more appropriate based on the actual usage (block 806). Then, it can be determined where additional devices 104 (i.e., the devices 104 that will expire) can be used prior to their expiration (block 808). The excess devices 104 can be sent to another department where they can be used prior to their expiration (block 810). Finally, the actual inventory level of the initial department is adjusted to reflect that the sent devices 104 are no longer available for consumption within the initial department (block 812). Thus, according to exemplary embodiments of the present invention, rather than sending new devices 104 to a department and allowing other devices 104 to expire, devices 104 that are to expire are used and waste is reduced.

According to an alternative exemplary embodiment, by recognizing that devices 104 in the local inventory (e.g., local inventory 610) have expired, a waste rate can be computed. Specifically, because some devices 104 were contained within the local inventory 610 and were not used because they expired, they were thus wasted. By comparing the number of devices 104 that were dispatched to the local inventory 610 and the number of devices 104 that were used, the number of devices 104 that were wasted (i.e., not used and expired) can be determined. Based on the waste rate calculation, the predetermined local inventory level can be recalculated to reduce or otherwise modify the waste rate. The new predetermined local inventory level can then be updated in, for example, the database 312 of the central repository 302.

According to another exemplary embodiment of the present invention, it is desirable to make certain devices 104 unavailable for use. For example, if a device 104 has expired due to having exceeded the room temperature or ambient storage time, the device 104 should not be used. FIG. 9 illustrates a flow chart for "locking out" devices 104, in accordance with exemplary embodiments of the present invention. Initially, an indication of when certain devices 104 have been removed from the refrigerator is provided to the reading apparatus 102 (block 902). Based on the indication, the reading apparatus 102 can determine when the removed devices 104 will expire due to exposure to ambient or room temperature. Such a determination can be based on direct information (e.g., the removed devices 104 will expire on a particular date), or computed information (e.g., the removed devices 104 will expire a certain amount of time from the date that they were removed from the refrigerator, depending on factors such as, for example, the actual ambient or room temperature). It can then be determined whether the ambient or room temperature timing for the removed devices 104 has elapsed (block 904). If the ambient or room temperature timing has not elapsed, then control returns to block 904 and the reading apparatus 102 continues to monitor whether the ambient or room temperature timing has elapsed. If the ambient or room temperature timing has elapsed, then the reading apparatus 102 locks out the expired devices 104 (block 906). Because the expired devices 104 are locked out, the expired devices 104 are not used. Thus, exemplary embodiments of the present invention can prevent devices 104 from being used that have expired.

The steps of a computer program as illustrated in FIGS. 4, 5 and 7-9 for controlling an inventory of a plurality of point-of-care diagnostic devices can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. As used herein, a "computer-readable medium" can be any means that can contain, store, communicate, propagate, or transport the program for use by or in connection with the instruction execution system, apparatus, or device. The computer-readable medium can be, for example but not limited to, an electronic, magnetic, optical, electromagnetic, infrared, or semiconductor system, apparatus, device, or propagation medium. More specific examples (a non-exhaustive list) of the computer-readable medium can include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CDROM).

It will be appreciated by those of ordinary skill in the art that the present invention can be embodied in various specific forms without departing from the spirit or essential characteristics thereof. The presently disclosed embodiments are considered in all respects to be illustrative and not restrictive. For example, it is to be understood that the present invention is applicable to other methods and apparatus for inventory management in a point-of-care system beyond sample testing devices. The scope of the invention is indicated by the appended claims, rather than the foregoing description, and all changes that come within the meaning and range of equivalence thereof are intended to be embraced.

All United States patents and patent applications, foreign patents and patent applications, and publications discussed above are hereby incorporated by reference herein in their entireties to the same extent as if each individual patent, patent application, or publication was specifically and individually indicated to be incorporated by reference in its entirety.

What is claimed is:

1. A point of care testing device comprising:
an analysis component configured to perform at least one sample analysis; and
a time indicator configured to:
provide a first code or signal associated with the device that indicates a first time when the device is transferred from a controlled main inventory to an ambient temperature subinventory; and
provide a second code or signal associated with the device that indicates a second time prior to the device performing said at least one sample analysis,
wherein a comparison between a predetermined ambient shelf life of the device and a time difference between said first time and said second time provides an indication of whether the device has expired; and
said predetermined shelf life provides a usable lifetime of the device at ambient temperature.

2. A point of care testing system comprising:
a disposable device comprising:
a port configured to receive a patient sample; and
a time indicator configured to:
provide a first code or signal associated with the disposable device that indicates a first time at which the disposable device has been moved from a refrigerated storage condition to an ambient storage condition; and
provide a second code or signal associated with the disposal device that indicates a second time prior to the disposable device receiving said patient sample; and
a reusable reader comprising:
a port configured to receive said disposable device; and
an identification device configured to:
receive said first code or signal and said second code or signal;
determine a time difference between said first time and said second time;
compare said time difference to a predetermined ambient shelf life of the disposable device; and
when said time difference is greater than said predetermined ambient shelf life, provide an indication that a usable lifetime of the disposable device has expired.

3. The point of care testing system of claim 2, wherein:
said predetermined ambient shelf life provides the usable lifetime of the disposable device at a stored ambient temperature; and
said ambient storage condition is the stored ambient temperature.

4. The point of care testing system of claim 2, wherein:
said disposable device is a cartridge further comprising analytical elements including electrodes or optics for sensing analytes within said patient sample; and
said reusable reader further comprises electrical circuitry for operating said electrodes or said optics.

5. A point of care testing system comprising:
a disposable device comprising:
a port configured to receive a patient sample; and
a time indicator configured to provide a first code or signal associated with the disposable device that indicates a first time at which the disposable device has been moved from a refrigerated temperature to an ambient temperature; and
a reusable reader comprising:
a port configured to receive said disposable device; and
an identification device configured to:
receive said first code or signal;
determine a second time when the disposable device will expire due to exposure to said ambient temperature based on a predetermined ambient temperature expiration date assigned to the disposable device;
determine whether said second time has elapsed prior to use of the disposable device to determine whether an ambient temperature shelf life of the disposable device at the ambient temperature is exceeded; and
when said second time has elapsed, lock out the disposable device such that the disposable device is prevented from being used.

* * * * *